US010881813B2

United States Patent
Säll et al.

(10) Patent No.: US 10,881,813 B2
(45) Date of Patent: Jan. 5, 2021

(54) TUBULAR ROTATOR FOR A MEDICAMENT DELIVERY DEVICE AND A MEDICAMENT DELIVERY DEVICE CONTAINING THE SAME

(71) Applicant: CAREBAY EUROPE LTD, Sliema (MT)

(72) Inventors: Daniel Säll, Segeltorp (SE); Nikolaj Hautaviita, Bro (SE); Daniel Carlsson, Enskede (SE)

(73) Assignee: SHL MEDICAL AG, Zug (CH)

(*) Notice: Subject to any disclaimer, the term of this patent is extended or adjusted under 35 U.S.C. 154(b) by 266 days.

(21) Appl. No.: 16/061,054

(22) PCT Filed: Nov. 15, 2016

(86) PCT No.: PCT/EP2016/077726
§ 371 (c)(1),
(2) Date: Jun. 11, 2018

(87) PCT Pub. No.: WO2017/108272
PCT Pub. Date: Jun. 29, 2017

(65) Prior Publication Data
US 2018/0361082 A1    Dec. 20, 2018

(30) Foreign Application Priority Data

Dec. 21, 2015   (EP) .................................. 15201726

(51) Int. Cl.
*A61M 5/50*       (2006.01)
*A61M 5/20*       (2006.01)
*A61M 5/32*       (2006.01)

(52) U.S. Cl.
CPC ........ *A61M 5/5086* (2013.01); *A61M 5/2033* (2013.01); *A61M 5/3202* (2013.01);
(Continued)

(58) Field of Classification Search
CPC .............. A61M 5/5086; A61M 5/2033; A61M 2205/583; A61M 2205/582;
(Continued)

(56) References Cited

U.S. PATENT DOCUMENTS

| | | | | |
|---|---|---|---|---|
| 2013/0035642 | A1* | 2/2013 | Daniel ................ | A61M 5/3158 604/189 |
| 2015/0202376 | A1* | 7/2015 | Haupt .................... | A61M 5/24 604/189 |
| 2015/0335829 | A1* | 11/2015 | Giambattista ....... | A61M 5/3146 604/192 |

FOREIGN PATENT DOCUMENTS

| | | |
|---|---|---|
| EP | 2468334 A1 | 6/2012 |
| WO | 2009/040601 A1 | 4/2009 |

(Continued)

OTHER PUBLICATIONS

International Search Report and Written Opinion for Int. App. No. PCT/EP2016/077726, dated Jan. 19, 2017.

*Primary Examiner* — Bhisma Mehta
*Assistant Examiner* — Daniel Moore
(74) *Attorney, Agent, or Firm* — McDonnell Boehnen Hulbert & Berghoff LLP

(57) ABSTRACT

The present disclosure relates to a tubular rotator for a medicament delivery device having a medicament delivery member cover and a sensor arrangement, wherein the tubular rotator includes a guide structure arranged to convert linear motion of the medicament delivery member cover to rotational motion of the tubular rotator, and a profiled distal edge periphery arranged to interact with the sensor arrangement for actuating the sensor arrangement. Also provided is a medicament delivery device having such a tubular rotator.

20 Claims, 10 Drawing Sheets

(52) U.S. Cl.
CPC ............... *A61M 2005/2013* (2013.01); *A61M 2205/581* (2013.01); *A61M 2205/582* (2013.01); *A61M 2205/583* (2013.01)

(58) Field of Classification Search
CPC .... A61M 2205/581; A61M 2005/2013; A61M 5/3202; A61M 2005/31588; A61M 2005/3126; A61M 5/31581; A61M 5/3157
See application file for complete search history.

(56) References Cited

FOREIGN PATENT DOCUMENTS

| WO | 2010/098928 A1 | 9/2010 |
|----|----------------|--------|
| WO | 2011/123024 A1 | 10/2011 |
| WO | 2013077800 A1 | 5/2013 |
| WO | 2014/095424 A1 | 6/2014 |

* cited by examiner

TUBULAR ROTATOR FOR A MEDICAMENT DELIVERY DEVICE AND A MEDICAMENT DELIVERY DEVICE CONTAINING THE SAME

CROSS REFERENCE TO RELATED APPLICATIONS

The present application is a U.S. National Phase Application pursuant to 35 U.S.C. § 371 of International Application No. PCT/EP2016/077726 filed Nov. 15, 2016, which claims priority to European Patent Application No. 15201726.5 filed Dec. 21, 2015. The entire disclosure contents of these applications are herewith incorporated by reference into the present application.

TECHNICAL FIELD

The present disclosure generally relates to medical devices. In particular, it relates to a medicament delivery device.

BACKGROUND

When handling a medicament delivery device, it may be beneficial to provide a visual, tactile or audio indication to a user regarding the current state of a medicament delivery device. In the case of a disposable medicament delivery device it may for example be advantageous to know whether the dose has been administered and whether medicament administration has been fully completed. Information regarding the former can for example be obtained by inspecting the drug cartridge which may be visible through a window. However for some users, for example those with impaired vision, this is not a viable option.

Information regarding the latter is disclosed in WO2011123024, which discloses a medicament delivery device comprising a drive means configured to act on a medicament container for expelling a medicament, a holding means configured to hold the drive means in a pre-tensioned state, an activation means configured to interact with the holding means for releasing the drive means from the pre-tensioned state, wherein the device further comprises feedback means configured to interact both with the holding means and with the drive means for generating an audible and/or tactile and/or visual signal indicating that the medicament has been completely expelled.

The medicament delivery device disclosed in WO2011123024 may furthermore comprise a U-bracket that has an outer distal surface of the distal transversal end wall that may further have a protrusion, adapted to be guided through an opening, typically a through hole of the distal end wall of a tubular extension part and extends distally a predetermined distance over the outer surface of the tubular extension part. The distally extending protrusion may have a bright and/or different colour than the rest of the device for generating a visual signal. Thus, the protrusion will enable both a tactile and a visual signal when the U-bracket hits the distal end of the tubular extension part.

WO2011123024 does however not disclose any feedback means indicating that the medicament delivery device has been used after removal from the injection site especially if the dose was not fully completed, and which can be relied upon by essentially all type of users. Although this document discloses a window from which the drug may be inspected, as previously explained this may not be possible for some users. Moreover, inspection can be made manually in a tactile manner by controlling whether the tubular activation member has been locked out or not, but such an operation entails the risk of commencement of an unwanted drug administration in case the medicament delivery device is still unused.

SUMMARY

In view of the above, a general object of the present disclosure is to provide a tubular rotator for a medicament delivery device and a medicament delivery device comprising such a tubular rotator which solve or at least mitigate the problems of the prior art.

According to a first aspect of the present disclosure there is provided a tubular rotator for a medicament delivery device comprising a medicament delivery member cover and a sensor arrangement, wherein the tubular rotator comprises: a guide structure arranged to convert linear motion of the medicament delivery member cover to rotational motion of the tubular rotator, and a profiled distal edge periphery arranged to interact with the sensor arrangement for actuating the sensor arrangement.

The profiled distal edge periphery of the rotator is hence designed such that rotation of the tubular rotator allows actuation of the sensor arrangement.

When assembled in a medicament delivery device, the tubular rotator is able to actuate the sensor arrangement by a rotating motion obtained from interaction with a linearly displaceable medicament delivery member cover. In this manner, the sensor arrangement is able to detect at least one state of medicament administration. Depending on the structure of the profiled distal edge periphery information regarding several stages of medicament administration may be obtained. These stages may include commencement of medicament administration, finalisation of drug administration and attaining a final state of the medicament delivery device post medicament delivery.

In particular, the number of elevation level transitions and the position of the elevation level transitions relative to the sensor arrangement determine the ability to differentiate the different stages of medicament administration.

According to one embodiment the guide structure includes a first axial groove, a second axial groove connected to the first axial groove by a first slanting surface, and a third axial groove connected to the second axial groove by a second slanting surface, wherein the second axial groove is arranged centrally with respect to the first axial groove and the second axial groove.

According to one embodiment the profiled distal edge periphery arranged to interact with the sensor arrangement for converting rotational motion of the tubular rotator to linear motion of the sensor arrangement.

According to one variation the profiled distal edge periphery is configured and arranged to interact with the sensor arrangement for converting rotational motion of the tubular rotator to linear and rotational motion of the sensor arrangement. It may also be a further advantage that the profiled distal edge periphery is configured and arranged to interact with the sensor arrangement for transferring the rotational motion of the tubular rotator to the sensor arrangement.

According to a second aspect of the present disclosure there is provided a medicament delivery device comprising a housing having a proximal end and a distal end, a medicament delivery member cover received by and rotationally interlocked with the housing, wherein the medicament delivery member cover is axially displaceable between an extended position relative to the housing and a retracted position, wherein the medicament delivery member cover is biased towards the extended position, a plunger rod axially biased towards the proximal end of the housing, a tubular rotator according to the first aspect disclosed herein, wherein the tubular rotator is rotatable relative to the housing, and which tubular rotator is arranged to receive the plunger rod, and a sensor arrangement axially biased towards the proximal end of the housing, which sensor arrangement abuts the profiled distal edge periphery of the tubular rotator, wherein the tubular rotator is initially arranged in a first rotational position in the extended position of the medicament delivery member cover, in which first rotational position the tubular rotator is arranged to prevent axial displacement of the plunger rod, wherein the guide structure is arranged to allow the tubular rotator to rotate from the first rotational position to a second rotational position by axial displacement of the medicament delivery member cover towards the retracted position, thereby allowing release of the plunger rod, and wherein the guide structure is arranged to allow the tubular rotator to rotate to a third rotational position distinct from the first rotational position by axial displacement of the medicament delivery member cover from the retracted position to the extended position, wherein the profiled distal edge periphery is structured so that the sensor arrangement is axially displaced by rotation of the tubular rotator from the second rotational position to the third rotational position, thereby providing an indication of medicament administration.

An effect obtainable thereby is that an indication of the finalisation of medicament administration may be provided as feedback to a user. In particular, this feedback may also potentially be provided after the medicament delivery device has been removed from the injection site.

The sensor arrangement could for example provide a visual and/or tactile indication by means of its axial displacement, or it could actuate a first sensor which upon actuation could trigger visual, audio or tactile means for user feedback concerning the finalisation of a medicament administration.

According to one embodiment the medicament delivery member cover has a radial protrusion arranged to run in the first axial groove in the first rotational position of the tubular rotator, to run in the second axial groove in the second rotational position of the tubular rotator, and in the third axial groove in the third rotational position of the tubular rotator.

One embodiment comprises a distal end lid provided with a through-opening aligned with an axis defined by the sensor arrangement, wherein the sensor arrangement is arranged to extend through the through-opening only in the third rotational position of the tubular rotator. Visual and tactile feedback concerning the finalisation of medicament administration may thereby be provided.

According to one embodiment the profiled distal edge periphery has a distinct elevation level associated with the third rotational position.

One embodiment comprises a rotatable indicator disc provided with at least two visually distinct circle sectors, a distal end lid provided with an indicator disc opening for exposing only one circle sector at a time, and wherein the sensor arrangement is arranged to enable rotation of the indicator disc by axial displacement of the sensor arrangement such that one circle sector displayed in the indicator disc opening corresponds to one of the first rotational position, the second rotational position and the third rotational position of the tubular rotator, and another circle sector displayed in the indicator disc opening corresponds to another one of the first rotational position, the second rotational position and the third rotational position of the tubular rotator.

According to one variation the rotatable indicator disc is provided with three visually distinct circle sectors, wherein the sensor arrangement is arranged to enable rotation of the indicator disc by axial displacement of the sensor arrangement such that each circle sector displayed in the indicator disc opening corresponds to a respective one of the first rotational position, the second rotational position and the third rotational position of the tubular rotator.

It can thereby be indicated in which state the medicament delivery device is in, i.e. in a state prior to use indicated by a first of the circle sectors, in a medicament administration state, indicated by a second of the circle sectors, or in a final, used state, indicated by the a third of the circle sectors. A user may hence obtain information to this end from the indicator disc.

According to one embodiment the profiled distal edge periphery is provided with a distinct elevation level for each of the first rotational position, the second rotational position and the third rotational position.

One embodiment comprises a torsion spring arranged to torsionally bias the indicator disc, wherein the sensor arrangement is arranged to stepwise rotate the indicator disc by rotation of the tubular rotator to each of the second rotational position and the third rotational position.

One embodiment comprises a recording unit attachable to the distal end of the housing, wherein the recording unit includes a first sensor arranged to be actuated by the sensor arrangement by axial displacement of the sensor arrangement, and an indicator unit triggered by the actuation of the first sensor and arranged to indicate at least one stage of medicament administration.

According to one embodiment the first sensor is an electromechanical switch.

According to one embodiment the profiled distal edge periphery has the same elevation level for each of the first rotational position and the third rotational position of the tubular rotator and a distinct elevation level for the second rotational position.

One embodiment comprises a U-bracket received by the tubular rotator and arranged around the plunger rod, a first energy accumulation member arranged between the U-bracket and the distal end of the plunger rod, and an injection end member axially displaceable by the U-bracket, in the second rotational position of the tubular rotator, wherein the recording unit comprises a second sensor arranged to detect axial displacement of the injection end member.

According to one embodiment the indicator unit is configured to indicate commencement of medicament administration by the first sensor detecting axial displacement of the sensor arrangement and finalisation of medicament administration by the second sensor detecting axial displacement of the of the injection end member, and to provide an indication to maintain the medicament delivery device at the injection site for a predetermined amount of time after finalisation of medicament administration.

It is typically required that the medicament delivery device is maintained in position at the injection site until the expelled dose has been properly absorbed and the liquid pressure created by the injected dose has subsided in the injection site area. The indicator unit may therefore be configured to indicate that the medicament delivery device is to be maintained at the injection site until a predetermined time after the detection of the second sensor, for example 5-10 seconds. This facilitates for the user to become aware of when to remove the medicament delivery device from the injection site.

One embodiment comprises processing circuitry configured to determine whether a dose has been properly administered by determining an elapsed time between detection of axial displacement of the sensor arrangement and axial displacement of the injection end member and comparing the elapsed time with a reference elapsed time.

The elapsed time between the two detections is dependent of the structure into which the medicament is provided; for example, the denser structure of the body compared to that of air means that it will take longer to administer a dose into the body than into air. It can thereby be determined whether the full dose has been properly administered or not.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

Figure 1:
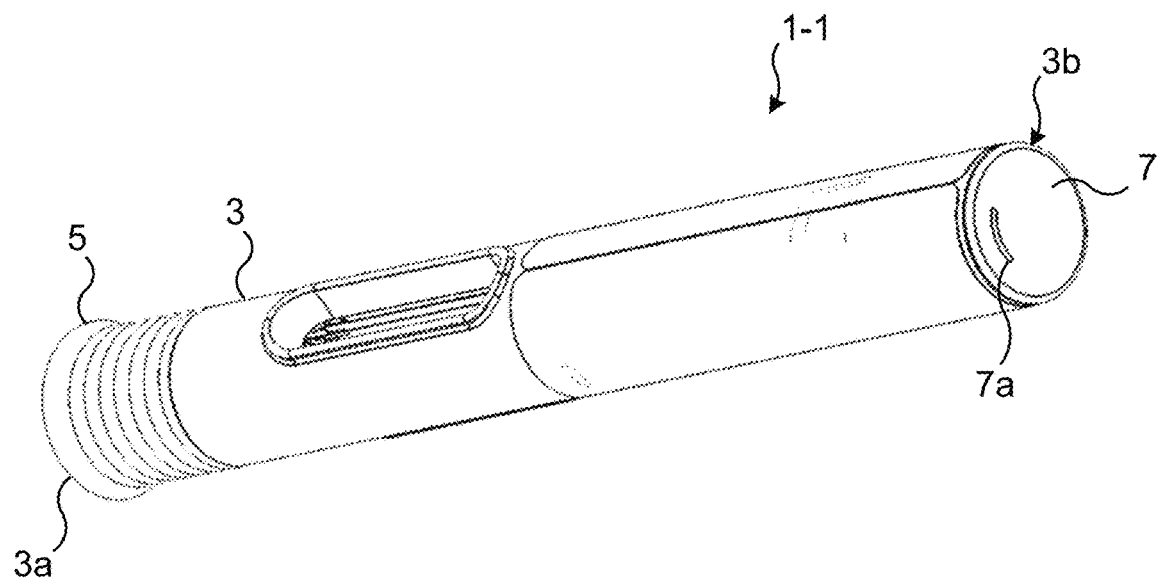
FIG. 1 shows a perspective view of a first example of a medicament delivery device.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein refers to that end of the medicament delivery device at which medical expulsion can be provided. This is hence that end of the medicament delivery device that is to be pointed towards the injection or expulsion site. This definition also extends to any internal or external component of the medicament delivery device, i.e. the proximal end of any component is that which is closest to the proximal end of the medicament delivery device. The "distal end" is the opposite end relative to the proximal end. With "proximal direction" is meant a direction from the distal end towards the proximal end, along the central axis of the medicament delivery device. With "distal direction" is meant the opposite direction to "proximal direction".

The medicament delivery device may for example a disposable single-use medicament delivery device, such as an auto-injector, an inhaler or an eye dispenser. The medicament delivery device may be a regular medicament delivery device for medicament administration, or a trainer device.

This disclosure concerns a medicament delivery device with user feedback capabilities. The medicament delivery device has a housing, a medicament delivery member cover received by the housing, rotationally interlocked with the housing, and which medicament delivery member cover is displaceable axially, between an extended position and a retracted relative to the housing, wherein the medicament delivery member cover is biased towards the extended position, an axially displaceable plunger rod, and a tubular rotator arranged to receive the plunger rod, and a sensor arrangement.

The tubular rotator is arranged to interact with the medicament delivery member, and has a guide structure arranged to convert linear motion of the medicament delivery member to rotational motion of the tubular rotator. The tubular rotator furthermore has a profiled distal edge periphery arranged to convert rotational motion of the tubular rotator to linear motion of the sensor arrangement. To this end, the profiled distal edge periphery is arranged to axially displace the sensor arrangement by rotation of the tubular rotator. In particular, the profiled distal edge periphery is designed such that this axial displacement of the sensor arrangement is performed when the tubular rotator rotates from a second rotational position to a third rotational position. The medicament delivery device is arranged to provide an indication to a user that medicament administration shifts from one state to another state based on the axial displacement of the sensor arrangement.

The tubular rotator is designed to allow distinction between different stages of medicament administration. To this end, the guide structure may have three axial grooves connected by respective slanting surfaces. This design provides essentially a two-tined fork-like groove structure or a Y-shaped groove structure arranged to engage with the medicament delivery member cover. The medicament delivery member cover has a corresponding radial protrusion arranged to run in only one of the three axial grooves at a time. The radial protrusion is initially arranged to run in a first tine, then during drug administration, in the "handle" portion, and upon finalisation of the drug administration, in the second tine. This sequence is ensured by the design of the slanting surface that guides the radial protrusion from the handle portion into the second tine. This engagement between the guide structure and the medicament delivery member cover enables the conversion of linear motion of the medicament delivery member cover to rotation of the tubular rotator.

With reference to FIG. 1 a first example of a medicament delivery device will now be described. Medicament delivery device 1-1 has a housing 3 and an administration end cover 5. The exemplified medicament delivery device 1-1 has a proximal end 3a and a distal end 3b, and a distal end lid 7 provided with a through-opening 7a.

Figure 2A:
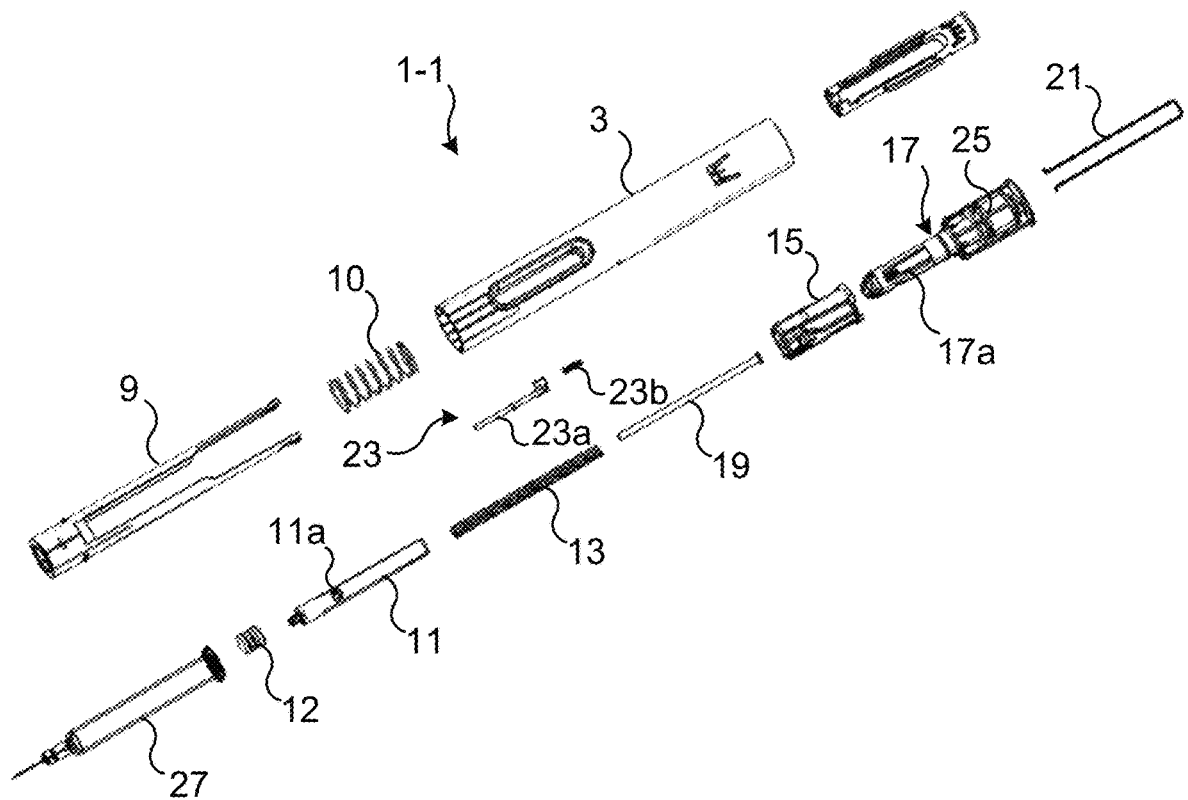
FIG. 2a depicts an exploded view of the medicament delivery device in FIG. 1.

FIG. 2a depicts an exploded view of the medicament delivery device 1-1 with most, however not all of its components shown. The medicament delivery device 1-1 further comprises a medicament delivery member cover 9, e.g. a needle cover, arranged to be received by the housing 3 and arranged to be biased in the proximal direction, a first energy accumulation member 10 arranged to bias the medicament delivery member cover 9 in the proximal direction, a plunger rod 11 which is arranged to be biased towards the proximal end 3a, a plunger 12, a second energy accumulation member 13 arranged to bias the plunger rod 11 in the proximal direction, which second energy accumulation member 13 may be a spring for example, a tubular rotator 15 arranged to receive the plunger rod 11 and the second energy accumulation member 13, a tubular extension part 17 which is axially and rotationally fixed relative to the housing 3, a rod 19 which the second energy accumulation member is arranged to receive, a U-bracket 21, and a sensor arrangement 23, which according to the present example includes a rod 23a that is arranged to be biased in the proximal direction.

The sensor arrangement 23 also includes an energy accumulating member 23b which can be integrated with the rod 23a or is distinct from the rod 23a, as shown in FIG. 2. The sensor arrangement 23 could alternatively be a switch, e.g. an electromechanical switch. The exemplified medicament delivery device 1-1 also includes a sensor arrangement holder 25 arranged to hold the sensor arrangement 23. Alternatively, the sensor arrangement and the sensor arrangement holder could have an integrated design.

According to the present example, the plunger rod 11 has an opening 11a, and the tubular extension part 17 which is arranged to receive the plunger rod 11 has a corresponding radial wing 17a flexible in the radial direction and arranged to engage with the opening 11a. The tubular rotator 15 is arranged to receive a portion of the tubular extension part 17, in particular that portion which comprises the radial wing 17a. In its initial position the tubular rotator 15 is arranged to push the radial wing into engagement with the opening 11 a preventing the plunger rod 11 from axial displacement. When the tubular rotator 15 is rotated, the inner structure of the tubular rotator 15 is designed such that it will provide less radial force on the radial wing 17a, allowing the radial wing 17a to flex radially outwards to disengage from the plunger rod 11. The plunger rod 11, which is biased in the proximal direction, is thereby displaced axially and medicament administration is thus initiated as the plunger rod 15 pushes the plunger 12 into a medicament container 27.

Figure 2B:
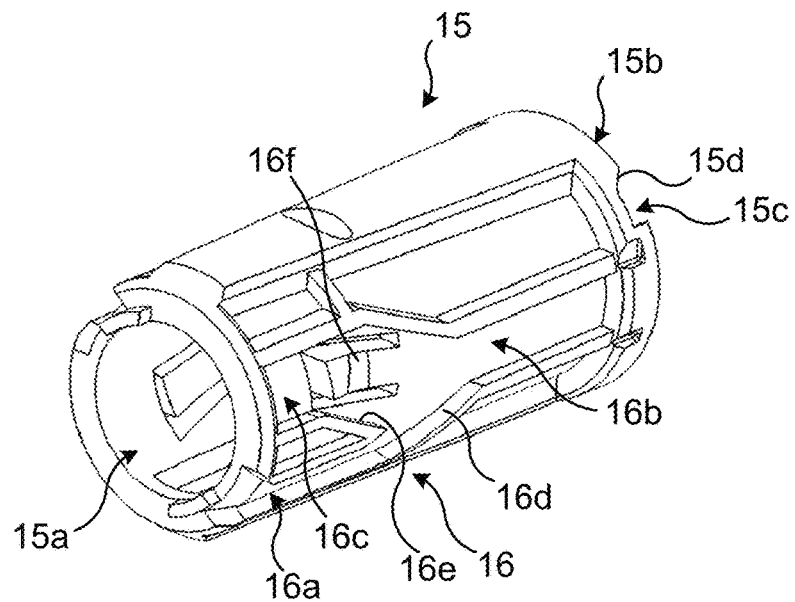
FIG. 2b shows a perspective view of an example of a tubular rotator for use in e.g. the medicament delivery device in FIG. 1.

Turning now to FIG. 2b an example of a tubular rotator 15 will now be described in more detail. Tubular rotator 15 has a central through-opening 15a extending from the proximal end to the distal end of the tubular rotator 15. The tubular rotator 15 is arranged to receive the tubular extension part 17 and the plunger rod 11 in the through-opening 15a.

The tubular rotator 15 furthermore has a profiled distal edge periphery 15b. The sensor arrangement 23 is arranged to abut the profiled distal edge periphery 15b. According to the present example, this means that the proximally biased rod 23a abuts the profiled distal edge periphery 15b. Due to it being biased, it can follow the profile of the profiled distal edge periphery 15b when the tubular rotator 15 rotates.

According to any example disclosed herein, the medicament delivery device may optionally include a second sensor arrangement identical to the sensor arrangement 23, for example arranged parallel with the sensor arrangement 23 and in a rotational symmetric manner e.g. at 180 degrees angle from the sensor arrangement 23. To this end, there may be two sensor arrangements 23 provided to detect rotation of the tubular rotator by detecting level changes of the profiled distal edge periphery 15b during rotation thereof.

The profiled distal edge periphery 15b includes at least one cut-out or indentation 15c, and/or elevated portion forming the profiled structure of the profiled distal edge periphery 15b. There are hence at least two elevation level transitions formed by the profiled distal edge periphery 15b. The profiled distal edge periphery 15b may beneficially be designed such that all level transition in the rotational direction of the tubular rotator 15 facilitates rotation. This is advantageous because the sensor arrangement 23 abuts the profiled distal edge periphery 15b and the interaction between the profiled tubular rotator and the sensor arrangement 23 should be as smooth as possible from a usability standpoint. The interaction between these components should provide minimal impact on the operation of the medicament delivery device 1-1. This may for example be obtained by providing slanting level transition surfaces, such as level transition surface 15d.

The tubular rotator 15 furthermore comprises a guide structure 16. The guide structure 16 is arranged to interact with the medicament delivery member cover 9, in particular to convert linear motion of the medicament delivery member cover 9 to rotational motion of the tubular rotator 15.

The guide structure 16 includes three connected axial grooves, namely a first axial groove 16a, a second axial groove 16b, and a third axial groove 16c. These three grooves 16a, 16b, 16c may have essentially a dual-tined fork shape, or Y-shape, with the two tines transitioning into a "handle" portion in the distal direction. The first axial groove 16a transitions into the second axial groove 16b via a first slanting surface 16d. The second axial groove 16b transitions into the third axial groove 16c via a second slanting surface 16e. The guide structure 16 may be provided on the outer surface of the tubular rotator 15, as shown in FIG. 2b, or it may alternatively be provided on the inner surface of the tubular rotator in which case the tubular rotator is designed with a larger radius than in the present example.

The tubular rotator 15 may be provided with two guide structures 16 of the type disclosed above, preferably arranged at about 180 degrees from each other, to obtain a rotational symmetric design with higher mechanical robustness in interaction with the medicament delivery member cover 9.

The tubular rotator 15 is also arranged to prevent linear displacement in the distal direction of the medicament delivery member cover 9 once the medicament delivery member cover 9 has reached the proximal end of the third axial groove 16c. To this end, the tubular rotator 15 may comprise a radial blocking member 16f, for example a snap-lock member which is radially flexible. The blocking member 16f may for example have a flexible ramp structure, increasing in radial height in the proximal direction. The blocking member 16f is arranged to allow the medicament delivery member cover 9 to run along the second slanting surface 16e and to transition from the second axial groove 16b into the third axial groove 16c, to the proximal end of the third axial groove 16c. As previously mentioned, the blocking member 16f is further arranged to prevent the medicament delivery member cover 9 from axial displacement in the distal direction once it has passed by the blocking member 16f. The medicament delivery member cover 9 will thereby be maintained in the extended position when medicament has been administered, ensuring that the medicament delivery member cannot be exposed and thus that the medicament delivery device cannot be reused.

Figure 3A:
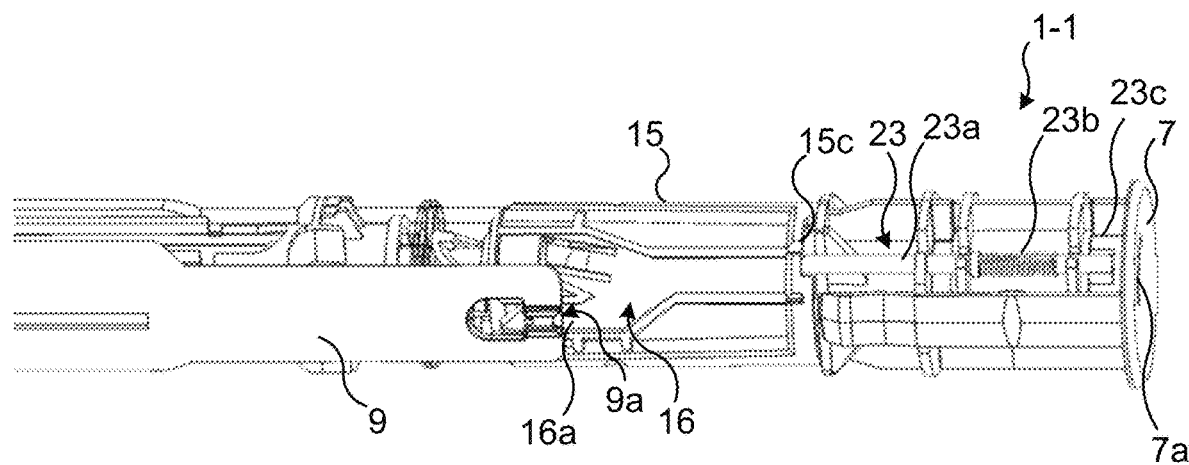
FIGS. 3a-c show side views, with the housing removed, of the medicament delivery device prior to medicament administration, during medicament administration, and post medicament administration.

FIG. 3a shows a portion of the medicament delivery device 1-1 without the housing 3, prior to commencement of medicament administration. The medicament delivery member cover 9 has a radial protrusion 9a, extending radially inwards, arranged in the first axial groove 16a of the tubular rotator 15 which is in a first rotational position in FIG. 3a. The medicament delivery member cover 9 is in the extended position. The sensor arrangement 23, in this example the rod 23a, is arranged in the cut-out 15c, at one end thereof, and abuts the profiled distal edge periphery 15b. The sensor arrangement 23 also includes an end member 23c linearly displaceable by the rod 23a. The rod 23a as well as the end member 23c is axially aligned with the through-opening 7a of the distal end lid 7. In this position, the end member 23c, in this example an indicator member, does not extend through the through-opening 7a.

Figure 3B:
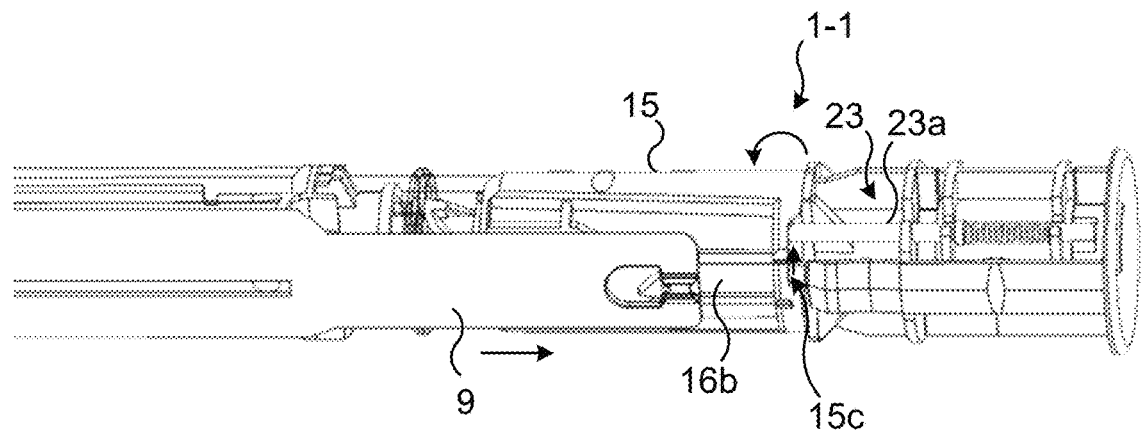

In FIG. 3b, the medicament delivery member cover 9 has been linearly displaced in the distal direction, from the extended position to a retracted position relative to the housing 3, and has interacted with the first slanting surface 16d such that the tubular rotator 15 has obtained a second rotational position. In this position, the radial protrusion of the medicament delivery member cover 9 is arranged in the second axial groove 16b. The sensor arrangement 23, in this case the rod 23a, has moved in the cut-out 15c to the other end thereof, due to the rotation of the tubular rotator 15.

Figure 3C:
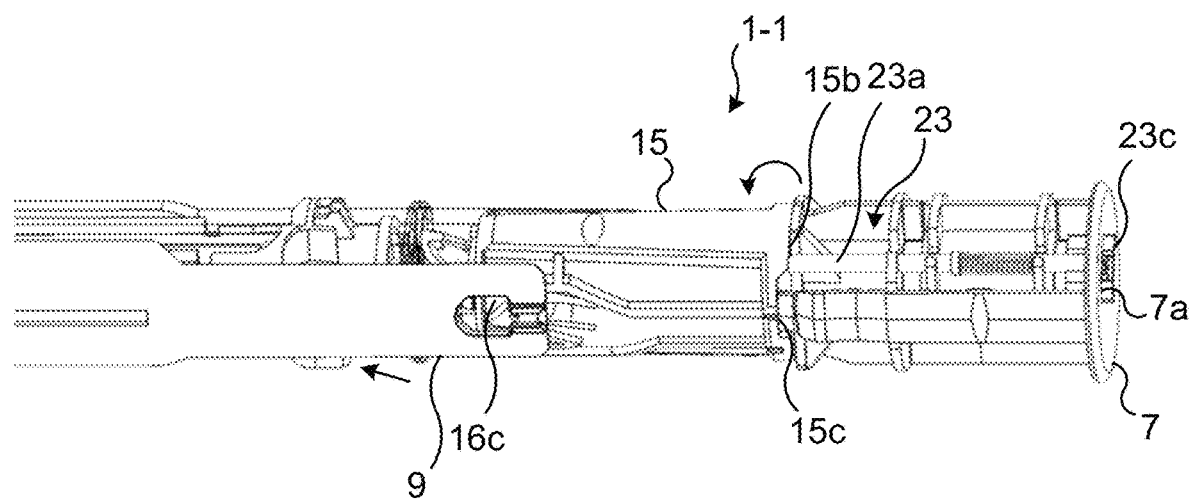

In FIG. 3c, the proximally biased medicament delivery member cover 9 has been released as the medicament administration has been finalised and hence returns to its extended position. The tubular rotator 15 has once again been rotated, this time to a third rotational position in which the radial protrusion of the medicament delivery member cover 9 has run along the third axial groove 16c. The sensor arrangement 23, in particular the rod 23a, has been axially displaced in the distal direction as the rod 23a followed the profiled distal edge periphery 15c when the tubular rotator 15 was rotated, and is now arranged outside the cut-out 15c. The end member 23c has thus been linearly displaced in the distal direction and now extends through the distal end lid 7, in particular through the through-opening 7a. The end member 23c provides tactile indication of use of the medicament delivery device 1-1. The end member 23c may optionally be provided with a visual indicator e.g. a distinct colour from the distal end lid 7, or a word such as "used", as shown in the example in FIG. 3c to provide a visual indication or feedback to a user that the medicament delivery device 1-1 has been used.

Figure 4:
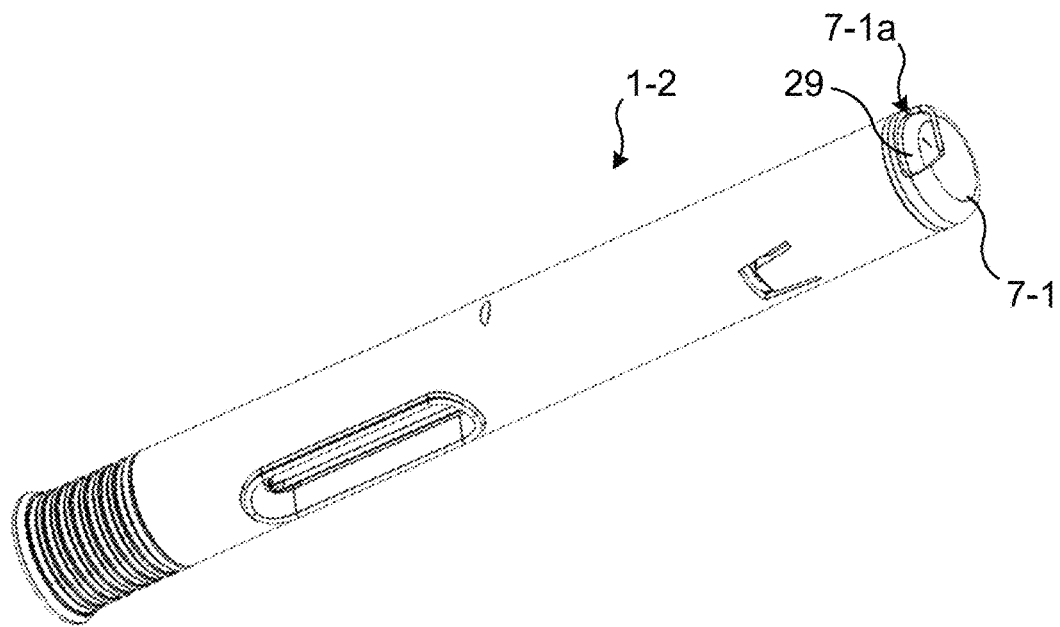
FIG. 4 is a perspective view of a second example of a medicament delivery device.

FIG. 4 shows a second example of a medicament delivery device. Medicament delivery device 1-2 is similar in structure to medicament delivery device 1-1, but the indication of the status of the medicament delivery device 1-2 is more advanced, and will be described in more detail in the following.

Medicament delivery device 1-2 is essentially identical to medicament delivery device 1-1, concerning most components, even when it comes to the tubular rotator 15 and the sensor arrangement 23. However, the tubular rotator of medicament delivery device 1-2 has a slightly different profiled distal edge periphery. Furthermore, medicament delivery device 1-2 has a distal end lid 7-1 that has a different through-opening, an indicator disc opening 7-1a. Medicament delivery device 1-2 also comprises an indicator disc 29. In the present embodiment, the indicator disc 29 is divided into three visually distinct circle sectors 29a, 29b, and 29c. The indicator disc 29 is furthermore torsionally biased. The indicator disc opening 7-1a is arranged to expose only one of the circle sectors 29a-c at a time. Each circle sector 29a-c is associated with a respective position of the first rotational position, the second rotational position and the third rotational position of the tubular rotator 15. Here, the tubular rotator 15 has three distinct levels of elevation at its profiled distal edge periphery, each associated with a respective one of the said rotational positions. Thus, as the tubular rotator 15 is rotated by linear displacement of the medicament delivery member cover 9, the sensor arrangement 23 is affected. In this example the sensor arrangement 23 is initially positioned at a highest elevation level of the profiled distal edge periphery, and is in each following rotational position lowered a step, i.e. displaced in the proximal direction, to lower elevation levels. The sensor arrangement 23 is thus stepwise displaced in the proximal direction. This enables stepwise rotation of the indicator disc 29 so that the circle sectors 29a-c are displayed through the indicator disc opening 7-1a of the distal end lid 7-1 in a subsequent order dependent of the rotational position of the tubular rotator 15.

Figure 5:
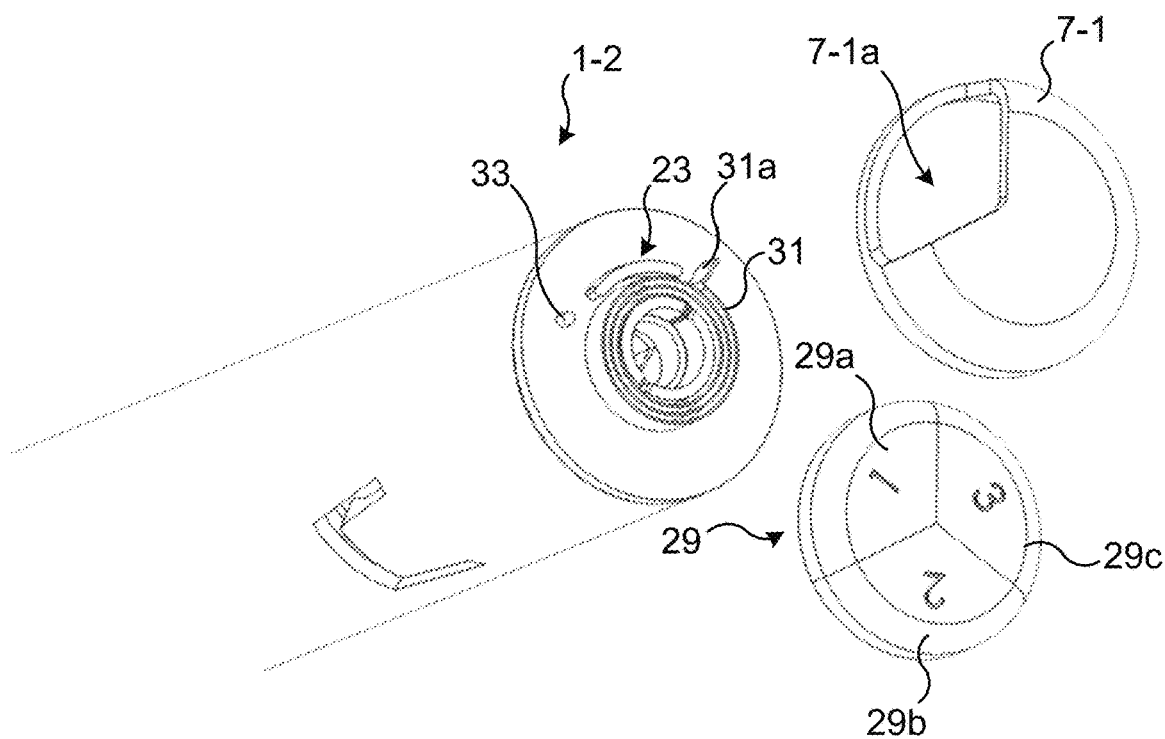
FIG. 5 shows a distal portion of the medicament delivery device in FIG. 4, with a distal end lid and an indicator disc removed.

As shown in FIG. 5, the torsional biasing may be provided by means of a torsion spring 31 which interacts with the indicator disc 29. The biasing may be obtained by a radial portion 31a of the torsion spring 31 which engages with the indicator disc 29. The medicament delivery device 1-2 may also comprise a stopper 33 arranged to prevent further rotation of the indicator disc 29 when the tubular rotator 15 has reached the third rotational position and the third circle sector 29c is displayed through the distal end lid 7-1.

Figure 6A:
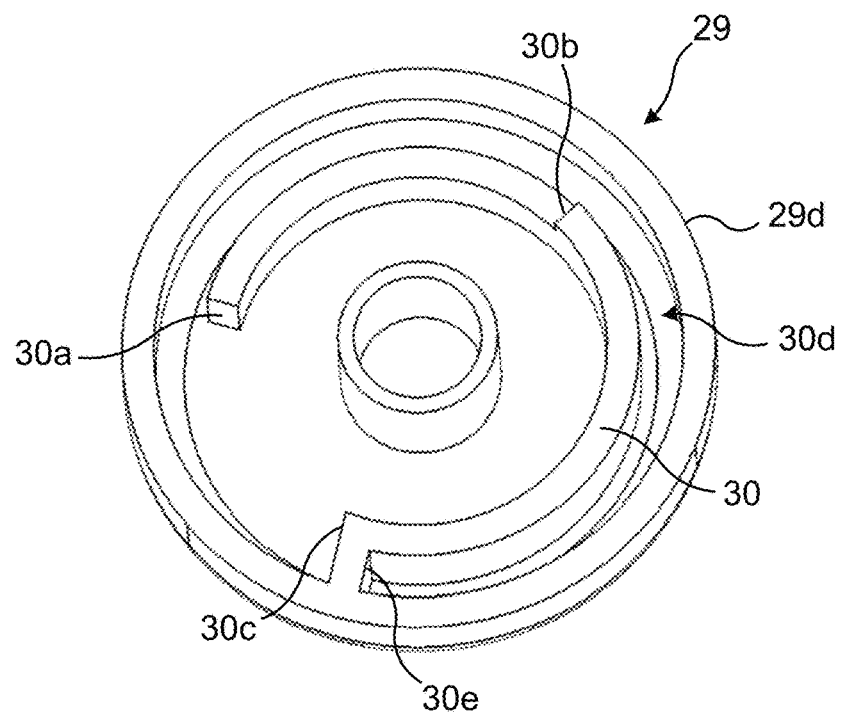
FIG. 6a shows the inner side of the indicator disc in FIG. 5.

FIG. 6a shows the indicator disc 29 from below, i.e. its inner surface. The indicator disc 29 has a tangentially extending inner wall 30 extending radially inwards and parallel with the peripheral outer wall 29d along the majority of the periphery of the indicator disc 29. The inner wall 30 is provided with two axial steps 30a and 30b arranged to interact with the linearly displaceable distal end of the sensor arrangement 23. A radial wall portion 30c engages with or bears against the radial portion 31a of the torsion spring 31 such that the torsional spring 31 can subject the indicator disc 29 to a torsional force.

A channel 30d is formed between the outer wall 29d of the indicator disc 29 and the inner wall 30. The channel 30d has an end wall 30e. The stopper 33 is arranged to run in this channel 30d. When the tubular rotator 15 reaches the third rotational position, the stopper 33 will bear against the end wall 30e thus preventing the indicator disc 29 from further rotation.

Figure 6B:
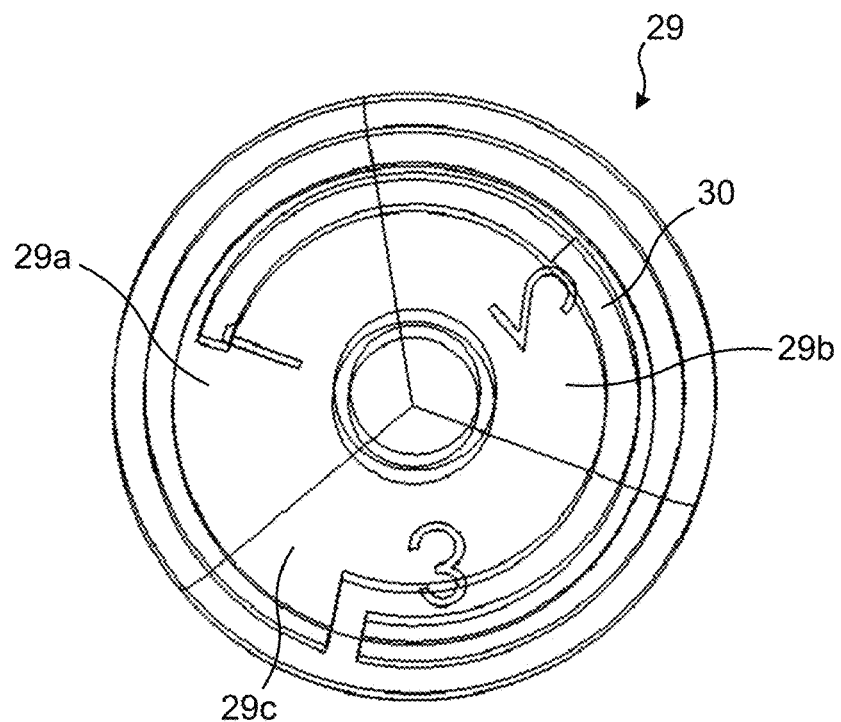
FIG. 6b shows the inner side of the indicator disc in FIG. 5 made transparent.

FIG. 6b shows a transparent view of the indicator disc 29 from below so that the circle sectors 29a-c can be seen in relation to the inner wall 30.

Figure 7A:
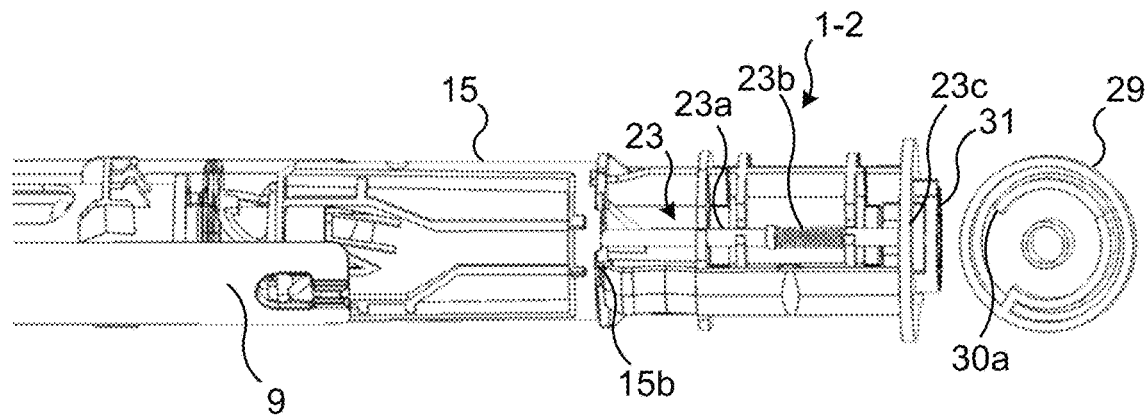
FIGS. 7a-c show side views, with the housing removed, of the medicament delivery device in FIG. 4, with the indicator disc rotated to depict the inner side thereof in operation.
Figure 7B:
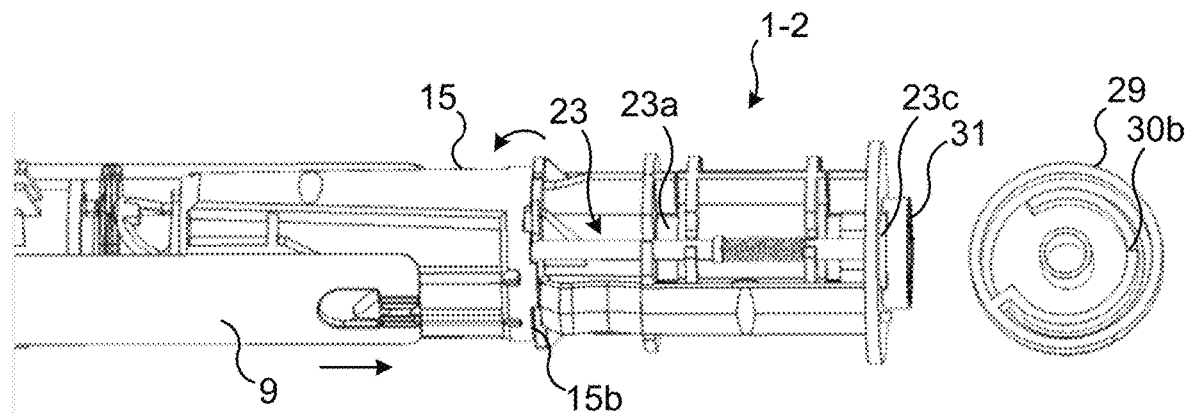
Figure 7C:
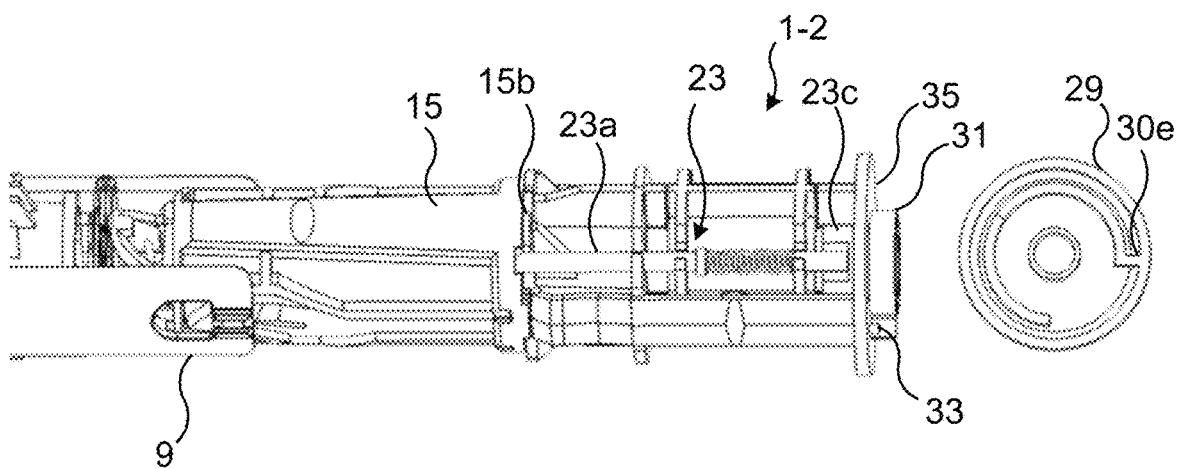

With reference to FIGS. 7a-c the operation of the medicament delivery device 1-2 will be described in more detail.

In FIG. 7a, the medicament delivery member cover 9 is in the extended position and the tubular rotator 15 is in the first rotational position as previously described. The sensor arrangement 23, in particular the rod 23, abuts the profiled distal edge periphery 15c of the tubular rotator 15. The profiled distal edge periphery 15b has a stair-like formation with the sensor arrangement 23 abutting the highest step or level of elevation in the first rotational position of the tubular rotator 15. The end member 23c hence extends below the indicator disc 29. In particular, the end member 23c abuts the axial step 30a, and the circle sector provided with a "1" is shown in the indicator disc opening 7-1a of the distal end lid 7-1.

In FIG. 7b, the medicament delivery member cover 9 is in the retracted position and the tubular rotator 15 is in the second rotational position. The tubular rotator 15 has thus been rotated and the sensor arrangement 23, in particular the rod 23a, has transitioned from the highest step to a lower step, the second highest step. The sensor arrangement 23 has thereby been moved a step in the proximal direction. A shorter portion of the end member 23c now extends in below the indicator disc 29. In this case, the sensor arrangement 23 abuts the axial step 30b and the indicator disc 29 has thus been rotated approximately 120 degrees. The circle sector with the number "2" will now be displayed in the indicator disc opening 7-1a of the distal end lid 7-1.

In FIG. 7c, the medicament delivery member cover 9 is again in the extended position and the tubular rotator 15 is in the third rotational position. The tubular rotator 15 has thus again been rotated and the sensor arrangement 23, in particular the rod 23a, has transitioned from the second highest step to a lower step. The sensor arrangement 23 has thereby been moved another step in the proximal direction. The end member 23c is now substantially level with or below the transverse surface 35 on which the torsion spring 31 is mounted. In this case, the indicator disc 29 has again been rotated approximately 120 degrees, this time stopped by the stopper 33 which now bears against the end wall 30e. The circle sector with the number "3" will now be displayed in the indicator disc opening 7-1a of the distal end lid 7-1.

In this manner, the user will be presented with information regarding the state in which the medicament delivery device 1-2 is in. In particular, three different states can be displayed by the indicator disc 29, namely prior to medicament administration, during medicament administration and post medicament administration, in the example corresponding to numbers "1", "2" and "3", respectively.

Figure 8:
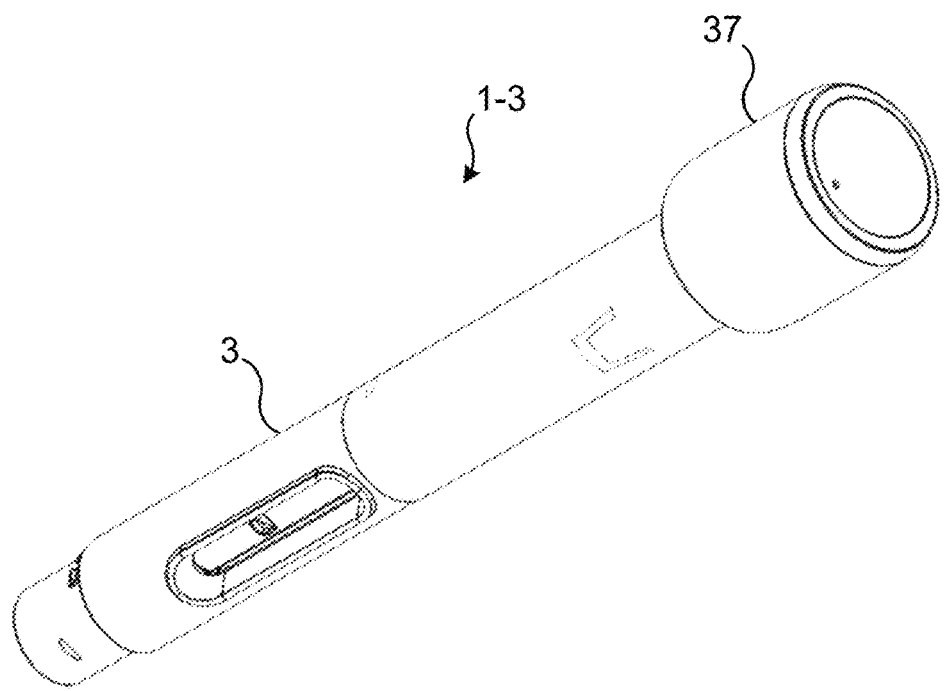
FIG. 8 is a perspective view of a third example of a medicament delivery device.

FIG. 8 shows a third example of a medicament delivery device. Medicament delivery device 1-3 is similar to the previously presented medicament delivery devices 1-1 and 1-2 when it comes to the structure of the tubular rotator 15 and the sensor arrangement 23. This third example however implements electromechanical aspects, and comprises a recording unit 37 provided with electronic components, and which recording unit 37 is attachable to and detachable from the housing 3.

The exemplified recording unit 37 is provided with one or more sensors 39-41. A first sensor 39 is arranged to be axially aligned with the sensor arrangement 23 when the recording unit 37 is assembled with the main body of the medicament delivery device 1-3. The first sensor 39 may for example be an electromagnetic switch.

The recording unit 37 may optionally include a second sensor 41, and/or a third sensor 43. The third sensor 43 is arranged to detect whether the recording unit 37 is attached to the main body of the medicament delivery device 1-3. This may trigger powering of the electronic components of the recording unit 37.

Figure 9A:
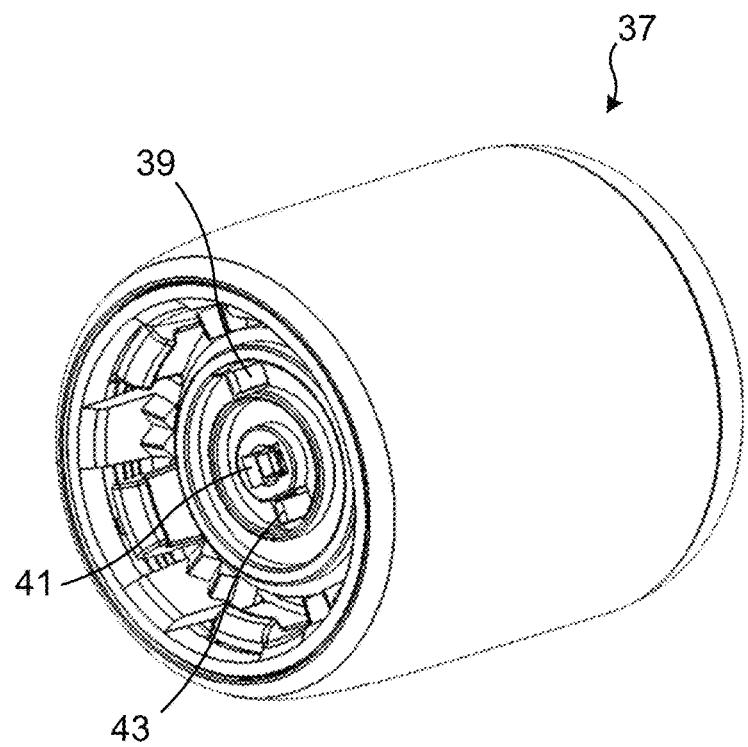
FIG. 9a shows an example of a recording unit of the medicament delivery device in FIG. 8.
Figure 9B:
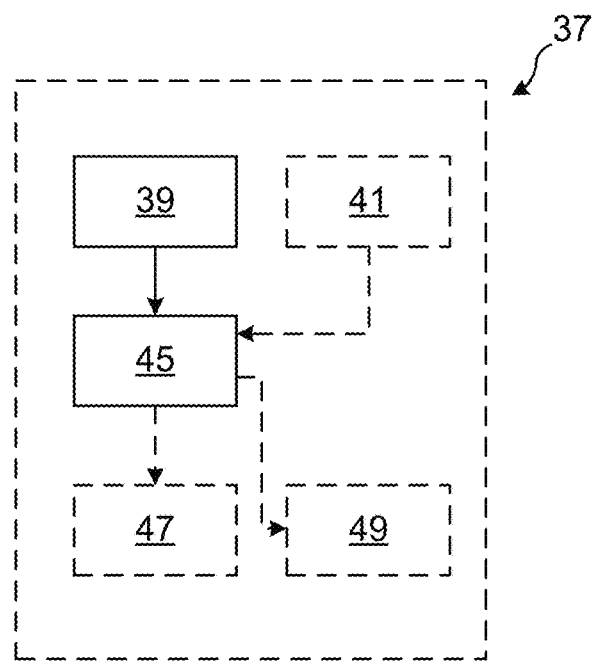
FIG. 9b is a block diagram showing a recording unit.

FIG. 9b shows a block diagram of electronic components of the recording unit 37. The recording unit 37 comprises the first sensor 39 configured to detect rotation of the tubular rotator 15, processing circuitry 45, and optionally an indicator unit 47 arranged to provide at least one of visual and audio feedback to a user regarding rotation detection by the first sensor 39. Visual feedback may for example be provided in the form of pulsating light from a light emitting diode (LED). The indicator unit 47 may thus according to one example include at least one LED.

The processing circuitry 45 is configured to obtain detection signals from the first sensor 39 The processing circuitry 45 uses any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations.

The recording unit 37 may according to one variation comprise a transmitter 49 arranged to wirelessly transmit detection data relating to a detection made by the first sensor 39, to an external device such as a smart device, e.g. a smart phone or a tablet computer, or to a personal computer to thereby provide user feedback from the external device. The transmitter 49 hence includes an antenna, which may be arranged to transmit the dose detection data over for example Bluetooth®, Wi-Fi™ or a cellular radio access network (RAN) such as Wideband Code Division Multiple Access (WCDMA) Long Term Evolution (LTE) and the 5G standard.

According to one variation, a unique identifier of the recording unit 37 may be transmitted with the detection data when a dose of medicament has been administered. This may facilitate compliance/adherence.

The recording unit 37 may furthermore comprise an energy storage unit. The energy storage unit may be configured to power the first sensor 39, and any other electronic component such as the processing circuitry 45, the indicator unit 47, and the transmitter 49, if present. The energy storage unit may for example be a battery.

Figure 10A:
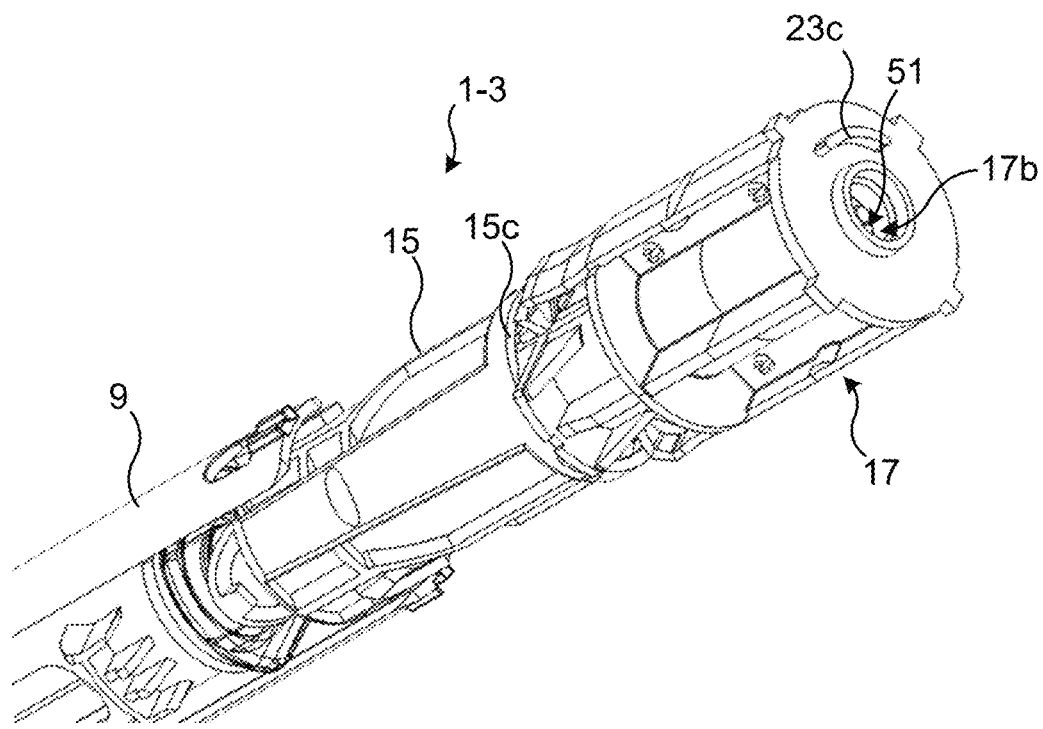
FIG. 10a shows a distal end portion of the medicament delivery device in FIG. 8 without the recording unit and housing.
Figure 10B:
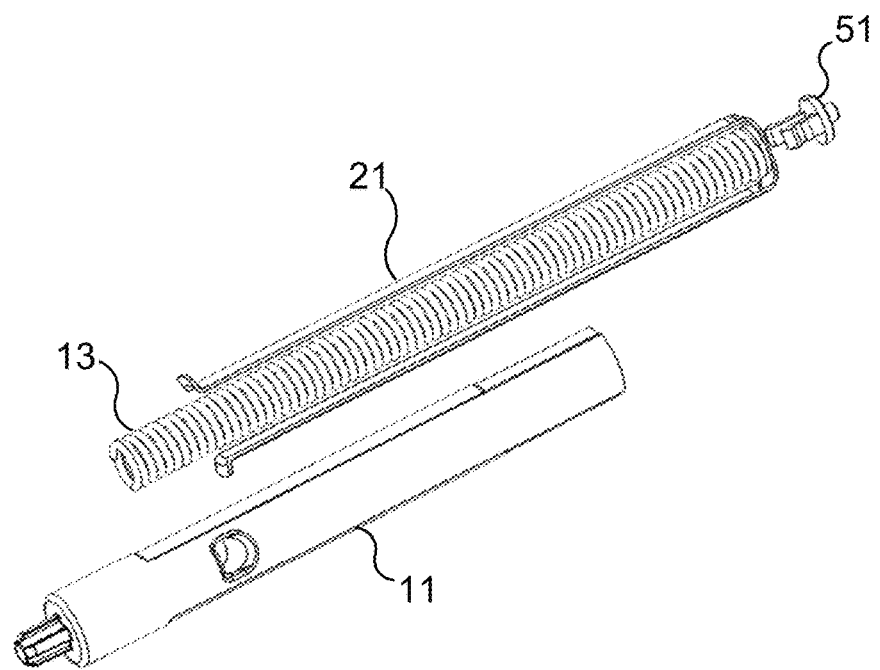
FIG. 10b shows a perspective view of a plunger rod and a U-bracket.

With reference to FIGS. 10a and 10b a variation comprising the second sensor 41 will now be described. According to this example the medicament delivery device 1 includes an injection end member 51 which is axially displaceable and arranged to interact with the U-bracket 21 shown in FIG. 10b. The tubular extension part 17 has a distal through-opening 17b in which the injection end member 51 is movably arranged. When a medicament has been fully administered, i.e. when the plunger rod 11 reaches its proximal end destination, the U-bracket 21 is released and due to the biasing provided by the first energy accumulation member 13, is pushed in the distal direction. As a result the injection end member 51 which is axially aligned and located distally relative to the U-bracket 21, is pushed axially in the distal direction by the U-bracket 21, as allowed by its free location in the distal through-opening 17b. The injection end member 51 will thereby actuate the second sensor 41 when the medicament has been fully expelled.

This feature in combination with the detection possibilities enabled by the first sensor 39 allows for very detailed feedback and information collection regarding medicament administration as will be further described in the following. In particular, it can provide details regarding correct or incorrect user handling of the medicament delivery device and even provide feedback to the manufacturer of the device regarding possible future design adjustments to further facilitate medicament administration for the user.

Figure 11A:
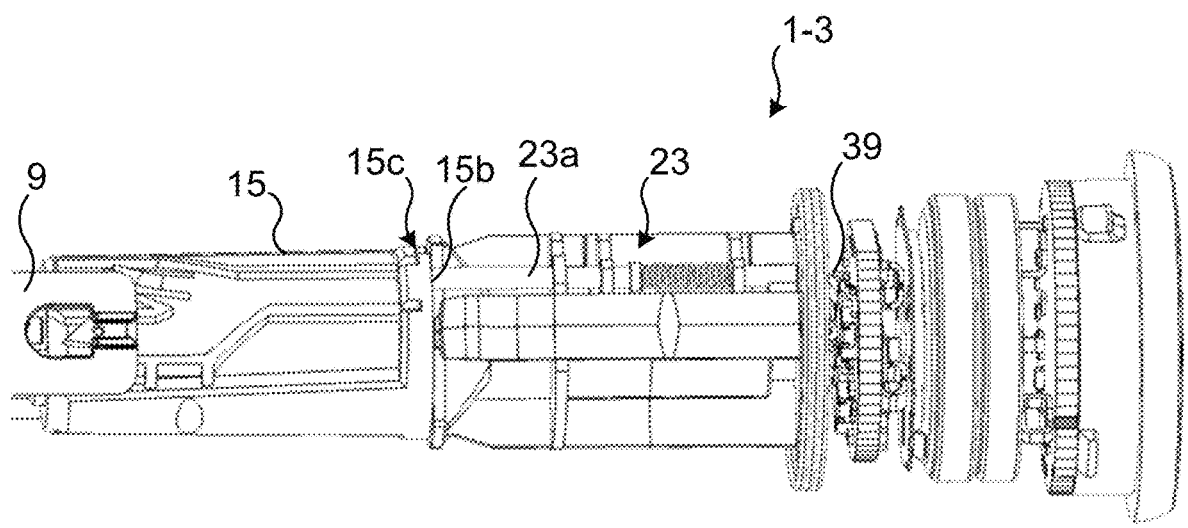
FIGS. 11a-c show side views, with the housing of the medicament delivery device and the recording unit removed, of the medicament delivery device in FIG. 8 in operation thereof

According to the present example, the profiled distal edge periphery 15b has one cut-out 15c for interaction with the sensor arrangement 23. As shown in FIG. 11a the sensor arrangement 23, in particular the rod 23a, abuts the profiled distal edge periphery 15c and is arranged outside the cut-out 15c when the medicament delivery member cover 9 is in the initial extended position and the tubular rotator 15 is in the first rotational position. The end member 23c shown in FIG. 10a is in this case fully extended and presses against the first sensor 39.

Figure 11B:
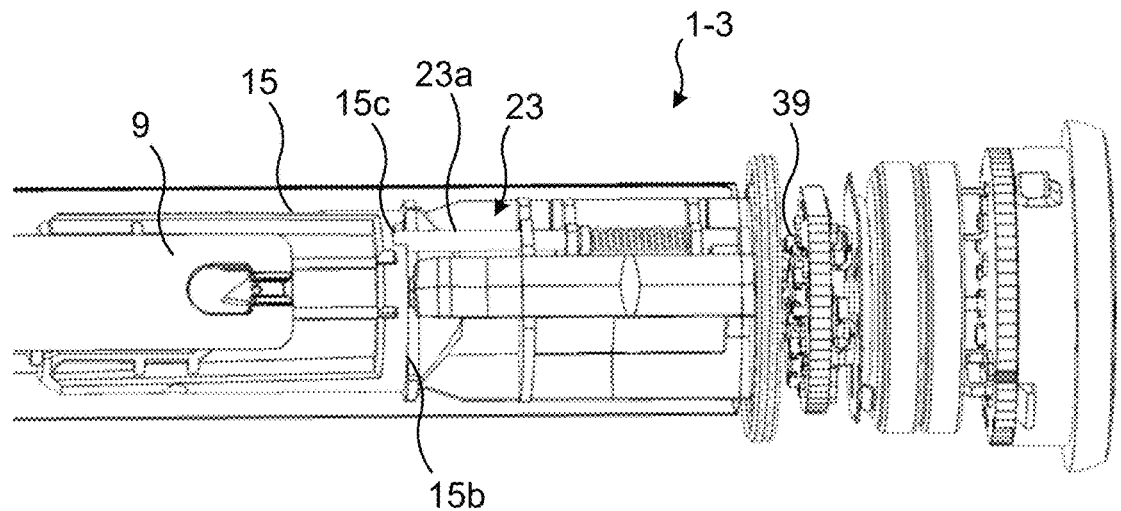

In FIG. 11b, the medicament delivery member cover 9 has been displaced and is now in the retracted position. The tubular rotator 15 has thus been rotated and is now in the second rotational position. As a result, the sensor arrangement 23 has been moved in the proximal direction as it has been received in the cut-out 15c of the profiled distal edge periphery 15b. The end member 23c has thus moved in the proximal direction and the first sensor 39 has thereby been actuated. The processing circuitry 45 now receives a detection signal from the first sensor 39 and may according to one variation trigger the indicator unit 47 to provide feedback e.g. by pulsating light. Alternatively, or additionally it may enable the transmitter 49 to transmit the detection data to an external device. The visual and/or audio feedback allows the user to understand that medicament administration has commenced.

Now, in case of a variation of the medicament delivery device 1-3 which comprises the injection end member 51 and the second sensor 41, the second sensor 41 will detect linear displacement of the injection end member 51 when the plunger rod 11 has reached its proximal end destination. The processing circuitry 45 may in this case be configured to instruct the indicator unit 47 to continue to provide visual and/or audio feedback to the user for a predetermined amount of time after the dose has been fully administered, corresponding to the time which is required to reduce the pressure in the injection site caused by the medicament.

Moreover, the processing circuitry 45 may according to one variation be configured to determine the elapsed time between detection by the first sensor 39 and detection by the second sensor 41 and to compare the elapsed time with a reference elapsed time. The processing circuitry 45 may then indicate by means of e.g. the indicator unit 47 whether the medicament delivery device 1-3 was held long enough to properly finalise the medicament administration, and/or or by transmitting this data by means of the transmitter 49 to an external device for feedback therefrom.

Figure 11C:
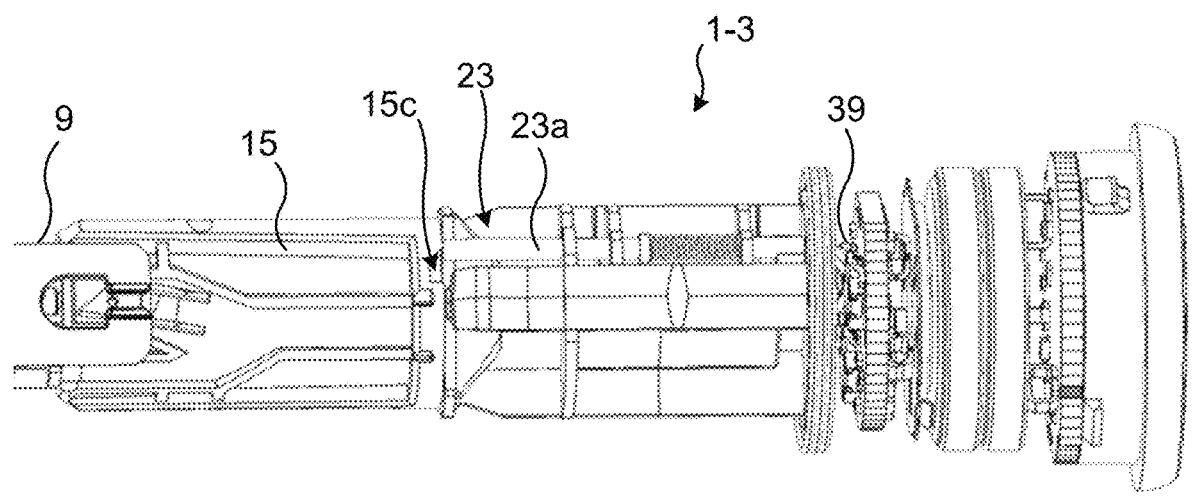

In FIG. 11c the medicament delivery member cover 9 has been released and is once again in the extended position. The tubular rotator 15 is in the third rotational position and the sensor arrangement 23, in particular the rod 23a, has been displaced in the distal direction as it has been moved out from the cut-out 15c. The first sensor 39 has thus once again been actuated by the end member 51. The processing circuitry 45 hence receives a detection signal from the first sensor 39, which is then able to instruct the indicator unit 47 to provide visual and/or audio feedback to this end.

In the manner described above, the medicament delivery device can provide feedback concerning a number of stages of medicament administration.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device comprising:
a housing having a proximal end and a distal end,
a medicament delivery member cover received by and rotationally interlocked with the housing, wherein the medicament delivery member cover is axially displaceable between an extended position relative to the housing and a retracted position, wherein the medicament delivery member cover is biased towards the extended position,
a plunger rod axially biased towards the proximal end of the housing,
a tubular rotator including a guide structure arranged to convert linear motion of the medicament delivery member cover to rotational motion of the tubular rotator, and a profiled distal edge periphery, wherein the tubular rotator is rotatable relative to the housing, and which tubular rotator is arranged to receive the plunger rod,
a sensor arrangement axially biased towards the proximal end of the housing, which sensor arrangement abuts the profiled distal edge periphery of the tubular rotator, and
a distal end lid provided with a through-opening aligned with an axis defined by the sensor arrangement,
wherein the tubular rotator is initially arranged in a first rotational position in the extended position of the medicament delivery member cover, in which first rotational position the tubular rotator is arranged to prevent axial displacement of the plunger rod,
wherein the guide structure is arranged to allow the tubular rotator to rotate from the first rotational position to a second rotational position by axial displacement of the medicament delivery member cover towards the retracted position, thereby allowing release of the of plunger rod,
wherein the guide structure is arranged to allow the tubular rotator to rotate to a third rotational position distinct from the first rotational position by axial displacement of the medicament delivery member cover from the retracted position to the extended position,
wherein the profiled distal edge periphery is structured so that the sensor arrangement is axially displaced by rotation of the tubular rotator from the second rotational position to the third rotational position, thereby providing an indication of medicament administration, and
wherein the sensor arrangement is arranged to extend through the through-opening only in the third rotational position of the tubular rotator.

2. The medicament delivery device as claimed in claim 1, wherein the medicament delivery member cover has a radial protrusion arranged to run in a first axial groove in the first rotational position of the tubular rotator, to run in a second axial groove in the second rotational position of the tubular rotator, and in a third axial groove in the third rotational position of the tubular rotator.

3. The medicament delivery device as claimed in claim 1, wherein the profiled distal edge periphery has a distinct elevation level associated with the third rotational position.

4. The medicament delivery device as claimed in claim 1, comprising a rotatable indicator disc provided with at least two visually distinct circle sectors, wherein the distal end lid is provided with an indicator disc opening for exposing only one of the at least two visually distinct circle sectors at a time, and wherein the sensor arrangement is arranged to enable rotation of the rotatable indicator disc by axial displacement of the sensor arrangement such that one of the at least two visually distinct circle sectors displayed in the indicator disc opening corresponds to one of the first rotational position, the second rotational position and the third rotational position of the tubular rotator, and another of the at least two visually distinct circle sectors displayed in the indicator disc opening corresponds to another one of the first rotational position, the second rotational position and the third rotational position of the tubular rotator.

5. The medicament delivery device as claimed in claim 4, wherein the profiled distal edge periphery is provided with a distinct elevation level for each of the first rotational position, the second rotational position and the third rotational position.

6. The medicament delivery device as claimed in claim 4, comprising a torsional spring arranged to torsionally bias the indicator disc, wherein the sensor arrangement is arranged to stepwise rotate the indicator disc by rotation of the tubular rotator to each of the second rotational position and the third rotational position.

7. The medicament delivery device as claimed in claim 1, comprising a recording unit attachable to the distal end of the housing, wherein the recording unit includes a first sensor arranged to be actuated by the sensor arrangement by axial displacement of the sensor arrangement, and an indicator unit triggered by the actuation of the first sensor and arranged to indicate at least one stage of medicament administration.

8. The medicament delivery device as claimed in claim 7, wherein the first sensor is an electromechanical switch.

9. The medicament delivery device as claimed in claim 7, wherein the profiled distal edge periphery has the same elevation level for each of the first rotational position and the third rotational position of the tubular rotator and a distinct elevation level for the second rotational position.

10. The medicament delivery device as claimed in claim 7, comprising a U-bracket received by the tubular rotator and arranged around the plunger rod, a first energy accumulation member arranged between the U-bracket and a distal end of the plunger rod, and an injection end member axially displaceable by the U-bracket, in the second rotational position of the tubular rotator, wherein the recording unit comprises a second sensor arranged to detect axial displacement of the injection end member.

11. The medicament delivery device as claimed in claim 10, wherein the indicator unit is configured to indicate commencement of medicament administration by the first sensor detecting axial displacement of the sensor arrangement and finalisation of medicament administration by the second sensor detecting axial displacement of the injection end member, and to provide an indication to maintain the medicament delivery device at an injection site for a predetermined amount of time after finalisation of medicament administration.

12. The medicament delivery device as claimed in claim 10, comprising processing circuitry configured to determine whether a dose has been properly administered by determining an elapsed time between detection of axial displacement of the sensor arrangement and axial displacement of the injection end member and comparing the elapsed time with a reference elapsed time.

13. A medicament delivery device comprising:
a housing having a proximal end and a distal end,
a medicament delivery member cover received by and rotationally interlocked with the housing, wherein the medicament delivery member cover is axially displaceable between an extended position relative to the housing and a retracted position, wherein the medicament delivery member cover is biased towards the extended position,
a plunger rod axially biased towards the proximal end of the housing,
a tubular rotator including a guide structure arranged to convert linear motion of the medicament delivery member cover to rotational motion of the tubular rotator, and a profiled distal edge periphery, wherein the tubular rotator is rotatable relative to the housing, and which tubular rotator is arranged to receive the plunger rod,
a sensor arrangement axially biased towards the proximal end of the housing, which sensor arrangement abuts the profiled distal edge periphery of the tubular rotator,
a rotatable indicator disc provided with at least two visually distinct circle sectors, and
a distal end lid provided with an indicator disc opening for exposing only one of the at least two visually distinct circle sectors at a time,
wherein the tubular rotator is initially arranged in a first rotational position in the extended position of the medicament delivery member cover, in which first rotational position the tubular rotator is arranged to prevent axial displacement of the plunger rod,
wherein the guide structure is arranged to allow the tubular rotator to rotate from the first rotational position to a second rotational position by axial displacement of the medicament delivery member cover towards the retracted position, thereby allowing release of the of plunger rod,
wherein the guide structure is arranged to allow the tubular rotator to rotate to a third rotational position distinct from the first rotational position by axial displacement of the medicament delivery member cover from the retracted position to the extended position,
wherein the profiled distal edge periphery is structured so that the sensor arrangement is axially displaced by rotation of the tubular rotator from the second rotational position to the third rotational position, thereby providing an indication of medicament administration, and
wherein the sensor arrangement is arranged to enable rotation of the rotatable indicator disc by axial displacement of the sensor arrangement such that one of the at least two visually distinct circle sectors displayed in the indicator disc opening corresponds to one of the first rotational position, the second rotational position and the third rotational position of the tubular rotator, and another of the at least two visually distinct circle sectors displayed in the indicator disc opening corresponds to another one of the first rotational position, the second rotational position and the third rotational position of the tubular rotator.

14. The medicament delivery device as claimed in claim 13, wherein the profiled distal edge periphery is provided with a distinct elevation level for each of the first rotational position, the second rotational position and the third rotational position.

15. The medicament delivery device as claimed in claim 13, comprising a torsional spring arranged to torsionally bias the indicator disc, wherein the sensor arrangement is arranged to stepwise rotate the indicator disc by rotation of the tubular rotator to each of the second rotational position and the third rotational position.

16. A medicament delivery device comprising:
a housing having a proximal end and a distal end,
a medicament delivery member cover received by and rotationally interlocked with the housing, wherein the medicament delivery member cover is axially displaceable between an extended position relative to the housing and a retracted position, wherein the medicament delivery member cover is biased towards the extended position,
a plunger rod axially biased towards the proximal end of the housing,
a tubular rotator including a guide structure arranged to convert linear motion of the medicament delivery member cover to rotational motion of the tubular rotator, and a profiled distal edge periphery, wherein the tubular rotator is rotatable relative to the housing, and which tubular rotator is arranged to receive the plunger rod,
a sensor arrangement axially biased towards the proximal end of the housing, which sensor arrangement abuts the profiled distal edge periphery of the tubular rotator,
a recording unit attachable to the distal end of the housing, wherein the recording unit includes a first sensor arranged to be actuated by the sensor arrangement by axial displacement of the sensor arrangement, and
an indicator unit triggered by the actuation of the first sensor and arranged to indicate at least one stage of medicament administration,
wherein the tubular rotator is initially arranged in a first rotational position in the extended position of the medicament delivery member cover, in which first rotational position the tubular rotator is arranged to prevent axial displacement of the plunger rod,
wherein the guide structure is arranged to allow the tubular rotator to rotate from the first rotational position to a second rotational position by axial displacement of the medicament delivery member cover towards the retracted position, thereby allowing release of the of plunger rod,
wherein the guide structure is arranged to allow the tubular rotator to rotate to a third rotational position distinct from the first rotational position by axial displacement of the medicament delivery member cover from the retracted position to the extended position,
wherein the profiled distal edge periphery is structured so that the sensor arrangement is axially displaced by rotation of the tubular rotator from the second rotational position to the third rotational position, thereby providing an indication of medicament administration, and
wherein the profiled distal edge periphery has the same elevation level for each of the first rotational position and the third rotational position of the tubular rotator and a distinct elevation level for the second rotational position.

17. The medicament delivery device as claimed in claim 16, wherein the first sensor is an electromechanical switch.

18. The medicament delivery device as claimed in claim 16, comprising a U-bracket received by the tubular rotator and arranged around the plunger rod, a first energy accumulation member arranged between the U-bracket and a distal end of the plunger rod, and an injection end member axially displaceable by the U-bracket, in the second rotational position of the tubular rotator, wherein the recording unit comprises a second sensor arranged to detect axial displacement of the injection end member.

19. The medicament delivery device as claimed in claim 18, wherein the indicator unit is configured to indicate commencement of medicament administration by the first sensor detecting axial displacement of the sensor arrangement and finalisation of medicament administration by the second sensor detecting axial displacement of the injection end member, and to provide an indication to maintain the medicament delivery device at an injection site for a predetermined amount of time after finalisation of medicament administration.

20. The medicament delivery device as claimed in claim 18, comprising processing circuitry configured to determine whether a dose has been properly administered by determining an elapsed time between detection of axial displacement of the sensor arrangement and axial displacement of the injection end member and comparing the elapsed time with a reference elapsed time.

* * * * *